United States Patent
Hodgin et al.

(10) Patent No.: US 6,949,194 B2
(45) Date of Patent: Sep. 27, 2005

(54) DISPOSABLE CHROMATOGRAPHIC COLUMNS

(75) Inventors: Delwin D. Hodgin, Lincoln, NE (US); Dale A. Davison, Greenwood, NE (US)

(73) Assignee: Teledyne Isco, Inc., Lincoln, NE (US)

(*) Notice: Subject to any disclaimer, the term of this patent is extended or adjusted under 35 U.S.C. 154(b) by 293 days.

(21) Appl. No.: 10/389,626

(22) Filed: Mar. 14, 2003

(65) Prior Publication Data

US 2003/0173294 A1 Sep. 18, 2003

Related U.S. Application Data

(62) Division of application No. 09/920,124, filed on Aug. 1, 2001, now Pat. No. 6,565,745.

(51) Int. Cl.[7] ............................................. B01D 15/08
(52) U.S. Cl. ...................... 210/656; 210/635; 210/198.2; 210/2.32
(58) Field of Search ................................ 210/635, 656, 210/198.2, 232, 238, 282; 96/101, 105, 106

(56) References Cited

U.S. PATENT DOCUMENTS

| | | | | |
|---|---|---|---|---|
| 3,810,545 A | * | 5/1974 | Filz et al. ................. | 210/198.2 |
| 4,169,793 A | * | 10/1979 | Lockshaw ................... | 210/169 |
| 4,283,280 A | | 8/1981 | Brownlee ................... | 210/198.2 |
| 4,313,828 A | | 2/1982 | Brownlee ................... | 210/198.2 |
| RE31,974 E | | 8/1985 | Brownlee ................... | 210/198.2 |
| 4,787,971 A | * | 11/1988 | Donald ...................... | 210/198.2 |
| 4,882,052 A | * | 11/1989 | Peranio ...................... | 210/282 |
| 4,915,831 A | * | 4/1990 | Taylor ....................... | 210/232 |
| 4,986,909 A | * | 1/1991 | Rai et al. ................... | 210/198.3 |
| 5,015,374 A | * | 5/1991 | Mathieu et al. ............. | 210/232 |
| 5,037,544 A | * | 8/1991 | Snyder ....................... | 210/198.2 |
| 5,128,034 A | * | 7/1992 | Kool .......................... | 210/232 |
| 5,167,809 A | * | 12/1992 | Mann et al. .............. | 210/198.2 |
| 5,193,703 A | * | 3/1993 | Staats et al. ............ | 220/203.01 |
| 5,266,193 A | * | 11/1993 | Kimura et al. ........... | 210/198.2 |
| 5,324,426 A | * | 6/1994 | Joseph et al. ............. | 210/198.2 |
| 5,360,544 A | * | 11/1994 | Nakaso et al. .............. | 210/483 |
| 5,439,593 A | | 8/1995 | Price ......................... | 210/660 |
| 5,462,659 A | * | 10/1995 | Saxena et al. ........... | 210/198.2 |
| 5,470,487 A | * | 11/1995 | Staats et al. ................ | 210/767 |
| 5,486,288 A | * | 1/1996 | Stanford et al. ........... | 210/235 |
| 5,601,708 A | | 2/1997 | Leavesley ................ | 210/198.2 |
| 5,667,676 A | * | 9/1997 | Alaska ..................... | 210/198.2 |
| 5,693,223 A | * | 12/1997 | Yamada et al. .......... | 210/198.2 |
| 5,767,387 A | | 6/1998 | Wang ........................ | 73/23.21 |
| 5,792,943 A | | 8/1998 | Craig ........................ | 73/61.52 |
| 6,068,766 A | | 5/2000 | Van Davelaar .......... | 210/198.2 |
| 6,090,190 A | * | 7/2000 | Enhsen et al. ................ | 96/101 |
| 6,117,329 A | * | 9/2000 | Hargro ....................... | 210/656 |
| 6,123,837 A | * | 9/2000 | Wadsworth et al. .......... | 210/87 |
| 6,171,486 B1 | * | 1/2001 | Green et al. ............. | 210/198.2 |
| RE37,216 E | * | 6/2001 | Koslow ..................... | 210/232 |
| 6,387,256 B1 | * | 5/2002 | Tuvim ..................... | 210/198.2 |
| 6,398,953 B1 | * | 6/2002 | Hargro .................... | 210/198.2 |
| 6,436,284 B1 | | 8/2002 | Leavesley et al. ....... | 210/198.2 |
| 2001/0001452 A1 | | 5/2001 | Moon et al. ............. | 210/198.2 |
| 2001/0001455 A1 | | 5/2001 | Moon et al. ................ | 210/635 |
| 2001/0001456 A1 | | 5/2001 | Moon et al. ................ | 210/635 |
| 2001/0001460 A1 | | 5/2001 | Moon et al. ................. | 216/37 |
| 2001/0001474 A1 | | 5/2001 | Moon et al. ................... | 239/3 |

* cited by examiner

*Primary Examiner*—Ernest G. Therkorn
(74) *Attorney, Agent, or Firm*—Vincent L. Carney

(57) ABSTRACT

To make an inexpensive chromatographic column and perform chromatography with it, column walls and a column end with an inlet port are molded integrally from plastic and a snap-on end is molded integrally with an outlet port from plastic. A filter is placed in one end of the column and the column is filled with packing material up to the second end. A filter is placed on top of the packing and a snap-on end with a molded outlet port is snapped onto the body with linear motion until an interference fit is formed. As the body and snap-on end are moved together cantilever members formed integrally with the snap on end are bent outwardly by detent members until the detent members are captured by an opening in the cantilever members.

13 Claims, 5 Drawing Sheets

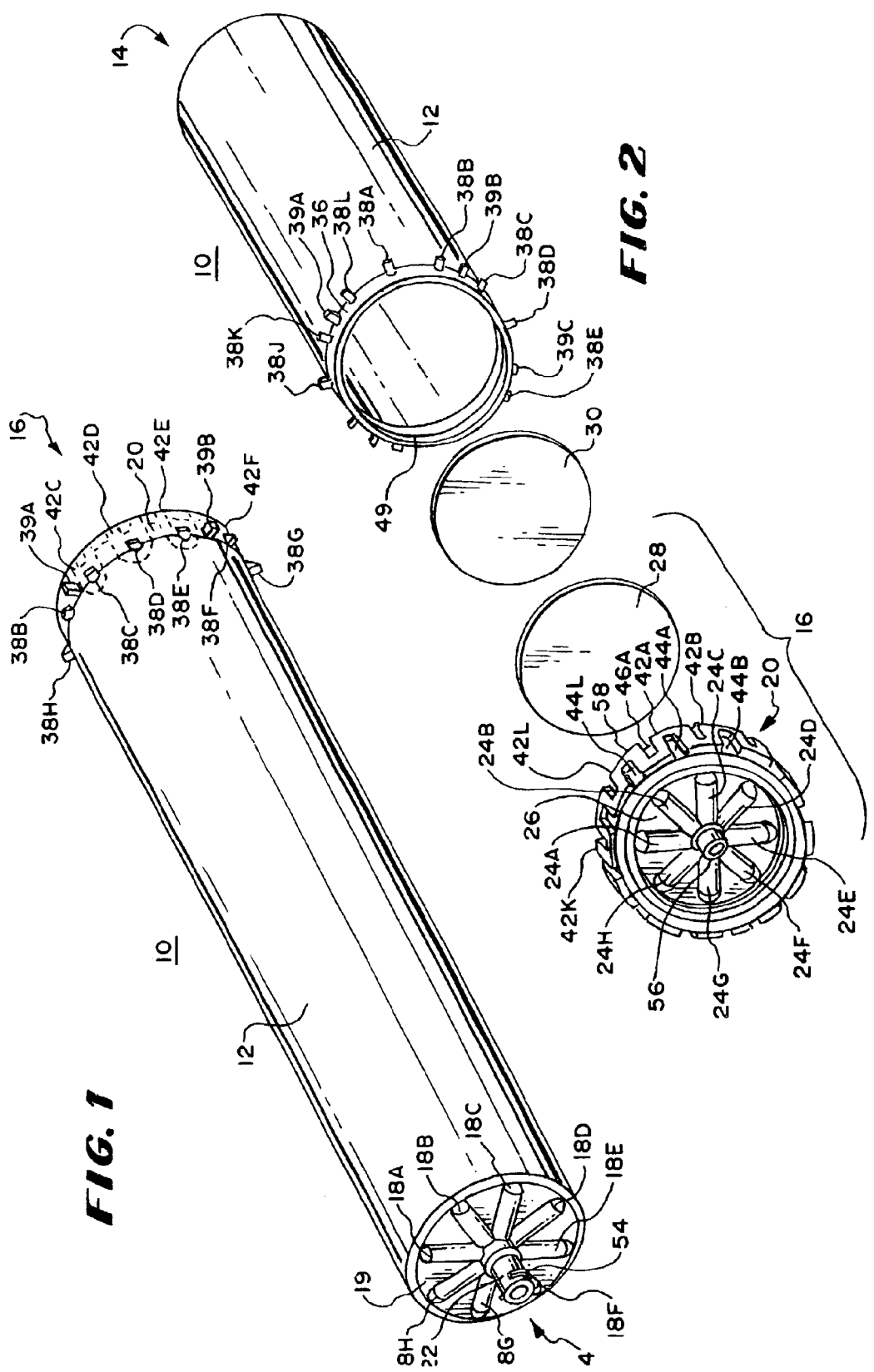

# DISPOSABLE CHROMATOGRAPHIC COLUMNS

RELATED CASE

This application is a divisional of U.S. application Ser. No. 09/920,124 filed Aug. 1, 2001 now U.S. Pat. No. 6,565,745 entitled DISPOSABLE CHROMATOGRAPHIC COLUMNS.

BACKGROUND OF THE INVENTION

This invention relates to chromatography and more specifically to chromatographic columns, methods of making chromatographic columns and methods of using chromatographic columns.

The use of chromatographic columns for the analysis and separation of substances from mixtures has long been known. One type of such column is a disposable column intended for limited use and accordingly manufactured with economy in mind.

One prior art disposable column has been available in commerce for a substantial period of time. It is manufactured of inexpensive plastics and designed to be easily assembled by filling the body of the column with the desired packing and then welding the open end or ends closed. The prior art chromatographic column has the disadvantage of being more costly then desirable to assemble and being more subject to leaks under pressure then desirable.

SUMMARY OF THE INVENTION

Accordingly, it is an object of the invention to provide a novel chromatographic column.

It is a further object of the invention to provide a novel method of manufacturing and using a chromatographic column.

It is a still further object of the invention to provide a novel chromatographic column that can be filled through an open end and then the open end closed with simple linear motion.

It is a still further object of the invention to provide a novel chromatographic column with a snap-on end.

It is a still further object of the invention to provide a novel inexpensive disposable chromatographic column.

In accordance with the above and further objects of the invention, a chromatographic column is formed of a relatively inexpensive material, filled with the desired packing material and then closed at one end without welding and nonetheless forming a seal that can withstand substantial pressure. In the preferred embodiment, the end is applied with relatively simple substantially linear motion so as to be capable of being implemented in an automated fashion and snaps in place to provide an adequate seal against internal pressures.

For this purpose, the column is formed of an inexpensive plastic with the tubular body portion and one end with one port being molded as a single piece. A snap-on end piece is also molded as a single piece with a port as an integrally molded part of it and snapped onto the tubular body portion with an interference fit adequate to resist leaks at a value above the rated value of the column. Preferably one of the end piece and the open end of the body of the column has snap members that engage detents on the other of the open end of the body and the end piece to hold the two together with adequate force about a tapered connection to form an adequate seal to resist the pressure built up on the column during use. The number of snaps and dimensions are selected to permit the appropriate inexpensive plastic to withstand the stress in use. In the preferred embodiment, the column is made substantially of polypropylene because it is inexpensive and sufficiently inert to withstand usage with normal solvents for a limited number of uses.

In molding the snap-on end and in molding the body a plurality of cantilever members are molded onto one of the body and the snap-on end and a plurality of detents are molded onto the other of the body and snap-on end. The number of detents and cantilever members are selected to maintain the combined bending stress of the cantilever members being bent outwardly over the catch and the tensile stress below the failure of the material comprising the cantilever members. The thickness of the material, the area connected the cantilever members to the rest of the end piece and the type of material are selected in conjunction with the height of the detent necessary to hold the cantilevers with the necessary force for an interference fit without excessively bending the cantilever members while being moved over the detents.

From the above description, it can be understood that the method and apparatus of this invention has several advantages, such as: (1) it is economical in terms of its fabricating materials; (2) it is inexpensive to assemble; (3) it can be assembled readily in an automated process; and (4) it can be easily formed of relatively inexpensive materials.

SUMMARY OF THE DRAWINGS

The above noted and further features of the invention will be better understood from the following detailed description when considered with reference to the accompanying drawings in which:

FIG. 1 is a perspective view of a column in accordance with the invention;

FIG. 2 is an exploded perspective view of the column of FIG. 1 viewed from another angle;

DESCRIPTION OF PREFERRED EMBODIMENTS

Figure 3:
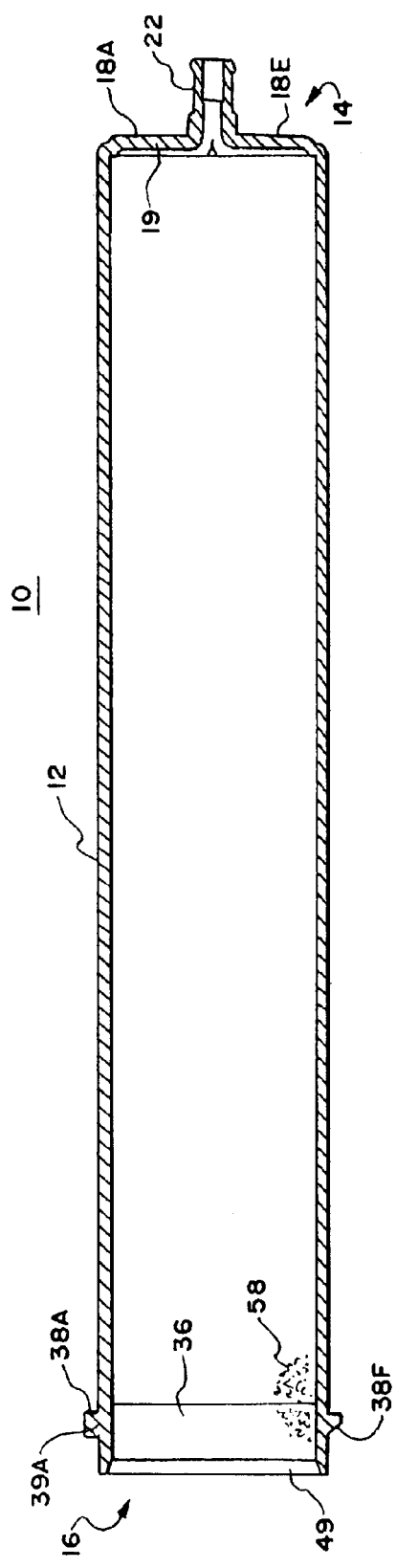
FIG. 3 is a longitudinal sectional view of the column of FIG. 1.

In FIG. 1, there is shown a column 10 having a column body 12, an inlet end 14 and an outlet end 16 with the direction of flow of fluid being from the inlet end through packing material 58 (FIG. 3) in the tubular column body 12 and out of the outlet end 16 in that order. The inlet end 14 includes a plurality of radially extending inlet channels 18A–18H, a base plate 19 and an inlet port 22. The inlet port includes a female luer connection partly threaded at 54 to connect to a source of fluid through a connector which in some embodiments may be spring-biased (not shown in FIG. 1) and extends as a hollow cylindrical tube through the center of the base plate 19 where it communicates with the inlet channels 18A–18H. The inlet port 22 does not require the use of wrenches or other tools to connect it to the source of fluid.

The inlet channels 18A–18H are formed in the base plate 19 and open toward the packing material 58 (not shown in FIG. 1) that fills the column body 12. The inlet channels 18A–18H extend radially from the inlet port 22 to the circumference of the base plate 19 and are angularly equally spaced from each other for the dispersion of fluid across the cross-section of packing material 58 within the column body 12 for more even flow through the packing material 58 within the column body 12 toward the outlet end 16. However, the inlet channels 18A–18H are not necessary for the proper operation of the column 10 nor to obtain the benefits of low cost and leak free operation.

The outlet end 16 includes a plurality of circumferentially-spaced detents 38A–38L (detents 38A–38G being shown in FIG. 1) and a plurality of circumferentially-spaced guide posts 39A–39F (39A and 39B being shown in FIG. 1) formed on the end of the column body 12 and cooperating with a plurality of cantilever members 42A–42L (42B–42F being shown in FIG. 1) to hold the cantilever assembly 20 in place on the outlet end 16. The outlet end 16 is closed by the snap-on cantilever assembly 20 and held firmly in place by detents 38A–38L (38A–38G being shown in FIG. 1) with a sealing relationship with the aid of the column body 12.

To bend the cantilever members 42A–42L and hold them in place, the radially extending detents 38A–38L extend outwardly from the outer wall of the column body 12 with which they are integrally formed and are circumferentially spaced from each other at equal intervals and positioned to be received by openings in the cantilever members 42A–42L when the cantilever members have been moved inwardly on the wall of the column body 12 a sufficient distance to a tapered rim of the walls (not shown in FIG. 1) so a matching portion of the ends of the cantilever members 42A–42L of the snap on cantilever assembly 20 have an interference fit with the tapered rim of the walls of the column body 12. They are positioned inwardly from the edge of the column body 12 a distance that cooperates with the snap-on cantilever assembly 20 to maintain an interference fit that seals against the escape of fluid except through the outlet port 56 (not shown in FIG. 1).

One of more guide posts 39A–39F (39A and 39B being shown in FIG. 1) are also molded on the column body 12 aligned in the same circumferential ring with the detents 38A–38L to aid in aligning the detents with the cooperating cantilever members 42A–42L of the snap-on cantilever assembly 20. The guide posts 39A–39F only fit between the cantilever members 42A–42L, and being located between detents 38A–38L, insure that the detents and cantilever members are in contact. They are at least equal in height to the detents 38A–38L. In the preferred embodiment the detents 38A–38L and guide posts are approximately 0.15 inches high and the cantilever members 42A–42L are 70 thousandths of an inch thick, the thickness of the cantilever members 42A–42L and height of the detents 38A–38L are selected to permit an adequate grip.

In this embodiment, the outlet end 16 is a snap-in place end and the inlet end 14 is molded integrally with the tubular column body 12. The column body 12, while cylindrical in the embodiment of FIG. 1 may have any cross-sectional shape suitable for chromatography and either the inlet end or the outlet end may be snapped on or both may be snapped on although it is economical to have one side molded and the other side open for convenient filling in one side and closing with a snap-on cover or other easily sealable cover.

In FIG. 2, there is shown an exploded perspective view of the column 10 having the outlet port 56, the snap-on cantilever assembly 20, outlet channels 24A–24H in cylindrical end plate 26, and the filters 28 and 30. The filter 30 is mounted at the inlet end 14 and the filter 28 at the outlet end 16. They may be any conventional material but in the preferred embodiment are formed as a disk from powdered plastic so as to be porous to the fluids in the mobile phase of the chromatographic process being used but able to block passage of packing material 58 from passing through them into the ports. The outlet channels 24A–24H are formed in the end plate 26 and have a semicircular cross section opening onto the packing material 58 within the column body 12 to aid in distributing the eluent from the cross section of the packing material 58 in the column body 12 to the outlet port 56.

The column body 12 is tapered slightly for ease in ejection of a mold during formation but has a straight portion 36 with the detents 38A–38L positioned to engage corresponding ones of a plurality of cantilever members 42A–42L at the outlet end 16 of the column 10. The radially-extending circumferentially-spaced detents 38A–38L are ramp shaped and mounted at the outer surface of the straight portion 36 of the column body 12 with the end nearest to the snap-on cantilever assembly 20 being lowest and sloping upwardly until they reach the top to aid in receiving the snap-fit cantilever assembly 20 and then falling sharply to provide a catching and holding surface to hold the cantilever assembly 20 at a location permitting an interference fit as will be described in greater detail below. The slope of the detents 38A–38L is selected to permit bending of the cantilever members 42A–42L without buckling. In the preferred embodiment, the slope is 20 degrees but may be between 5 and 45 degrees depending on the distance of travel desired before the cantilever members 42A–42L snap in place. The guideposts 39A, 39B and 39C have a steeply rising surface aligned with the low end of the ramp-shaped detents 38A–38L in the same circular cross section and are at least as high as the high end of the detents 38A–38L so they prevent movement of the cantilever assembly 20 onto the column body 12 unless the guide posts 39A–39F are positioned between cantilever members 42A–42L. With the guide posts 39A–39L positioned between cantilever members 42A–42L and inter-dispersed with the detents 38A–38L, the guide posts serve as guides to position the cantilever members 42A–42L with respect to the detents 38A–38L so the detents lift the cantilevers radially outwardly as the cantilever assembly 20 is moved on to the column body 12 until the cantilever members 42A–42L engage the end of the detents 38A–38L to hold the cantilever assembly 20 in place with an interference fit sealing the column body 12 of the column 10 to the cantilever assembly 20.

The outlet port 56 is formed integrally with the cantilever assembly 20. To provide an end seal, the end plate 26 of the cantilever assembly 20 includes a flat cylindrical torus ending in an integrally formed outlet port 56 and perpendicular to the londitudinal axis of the column body 12. At it circumferential end it rises in a direction substantially parallel to the walls of the column body 12 as a ring, curves and connects to the integrally formed cantilever members 42A–42L extending in the opposite direction. The rising walls have a sloped portion (not shown in FIG. 2) cooperates with the tapered rim 49 of the walls of the column body 12 to form an interference fit.

To collect fluid from the cross-section of the packing material 58 while preserving the integrity of the bands of migrating species, the snap cantilever assembly 20 includes a plurality of outlet channels 24A–24H which receive fluid from locations in the column body 12 of the column 10 and channel it to the outlet port 56. These channels are integrally formed with the end plate 26 and open inwardly toward the packing material 58 in the interior of the column body 12.

Circumferentially surrounding the end plate 26 and integrally formed with it is a sealing surface 36 (not shown in FIG. 2, see FIG. 7) extending substantially in the direction of the walls of the column body 12 and positioned to cooperate with the edge of the walls of the column body 12 to form a seal thereagainst. The cantilever members 42A–42L depend from the sealing surface 36 in the opposite direction so as to extend toward the detents 38A–38L, with each of the cantilever members 42A–42L having a central opening 44A–44L (44A, 44B and 44L shown here) and being separated from the others by corresponding cantilever longitudinal spaces 46A–46L (46A being shown here) forming U-shaped cantilever members 42A–42L each of which may be bent outwardly from the walls of the column body 12 by a corresponding one of the ramp-shaped detents 38A–38L in a manner to be described hereunder and receive the corresponding detent in the corresponding one of the openings 44A–44L.

With this arrangement, the filters 28 and 30 contain between them the packing material 58 (FIG. 3) and are between the molded inlet end 14 and snap-on outlet end 16 for the column body 12 of the column 10. The cantilever assembly 20 is forced linearly and axially onto the column body 12 with the cantilever members 42A–42L being bent outwardly by the ramp shaped detents 38A–38L and snapping over the detents 38A–38L to tightly pull the edge 48 of the walls of the column body 12 so that the rim 49 near the edge 48 is in an engaging position with a wall portion of the cantilever assembly 20 and thus to form a fluid tight seal between the tubular walls of the column body 12 and the cantilever assembly 20.

In the preferred embodiment, 12 cantilever member 42A–42L are used. However, the number of cantilever levers is chosen to be sufficient to avoid stress that will result in premature failure before the end of the useful life of the column. Stress on the cantilever at the point of holding and at the base is inversely proportional to the number of cantilever members since the pressure will be evenly distributed around the periphery during a chromatographic run. The shear strain on the cantilever members 42A–42L at the ends of the detents 38A–38L and the tensile strain on the cantilever side portions multiplied by the length of the side portions must be low enough not to reduce the pressure at the interference fit between the tapered rim of the walls of the body 12 and the sloped portion of the end plate 29 to permit leakage when the column is under pressure. The moment of inertia and flexural modules of the cantilever members must be low enough so that the cantilever assembly can be moved up the detent without excessive force and high enough to snap over the detent's peak and remain in place. The number of cantilever members (42A–42L in the preferred embodiment) and the size of the openings (44A–44L in the preferred embodiment) are selected to keep the stress below a value that causes premature failure or excessive elongation. In the preferred embodiment the material of the column body and the snap-fittings is polypropylene although many other materials can be used such as for example polyethylene or even metals since the choice of the material is based on cost. While in the preferred embodiment, the column is made of one material, different materials may be utilized, particularly to increase the rated pressure of a disposable column by incorporating parts of stronger plastic or metal reinforcing such as a reinforcing sleeve about the column body 12.

In FIG. 3 there is shown a longitudinal sectional view of a column 10 having a column body 12 with guide posts 39A–39F and detents 38A–38L (39A and 38A and 38F being shown in FIG. 3). As shown in this view, the inlet port 22 is integrally formed with its end piece and the body wall 12. The filter 30 (FIG. 2) is positioned at this end and held in place by the packing material 58, shown in fragmentary form in FIG. 3 but actually filling the column body 12 between the filters 28 and 30 (FIG. 2). The filter disc 30 prevents the packing material 58 from passing through the inlet port 22.

The column body 12 is molded of polypropylene manufactured by AMOCO and available from Polymerland Inc., Suite 150, 12200 Hebert Wayne Ct., Huntersville, N.C. 28078, as PP8439. However many other inexpensive materials may be used. In the preferred embodiment, one plastic is used for the entire column and the columns are intended for use at operating pressures of between gravity and 200 psi but a composite body such as with a strong sheath on the outside of the plastic body may extend operating pressures to 500 psi in a composite embodiment.

A tapered rim 49 is shown on the inner wall at the edge of the column body 12. This rim matches a surface on the cantilever assembly 20 and is tapered downwardly to the edge of the walls of the column body 12 so that as the cantilever assembly 20 is pressed onto the column body 12, the fit becomes increasingly tight until an interference fit is formed between the walls of the column body 12 and the cantilever assembly 20. The distance that the cantilever assembly must move onto the walls of the column body 12 is determined experimentally for each design of column and governs the amount and the length of the taper in conjunction with the location of the detents 38A–38L and the openings 44A–44L in the cantilever members 42A–42L to make a leak proof interference fit. In the preferred embodiment, the taper is 80 degrees from the plane of a perpendicular to the longitudinal axis of the body and there is mating 80 degree slope on the mating wall of the cantilever assembly 20. The total angle of the slope affecting the tightness of fit should be a value of between 5 degrees and 35 degrees in accordance the operating pressure.

Two of the inlet channels 18A and 18E of the channels 18A–18H are shown in this sectional view. As shown in this view, an outlet end 16 is open and available for inserting the packing material 58 prior to being closed by the snap-on cantilever assembly 20 to hold the packing material 58 and the filters 28 and 30 in place. The filter 28 (FIG. 2) prevents the packing material 58 from being carried into the outlet port 56 and affecting the system.

Figure 4:
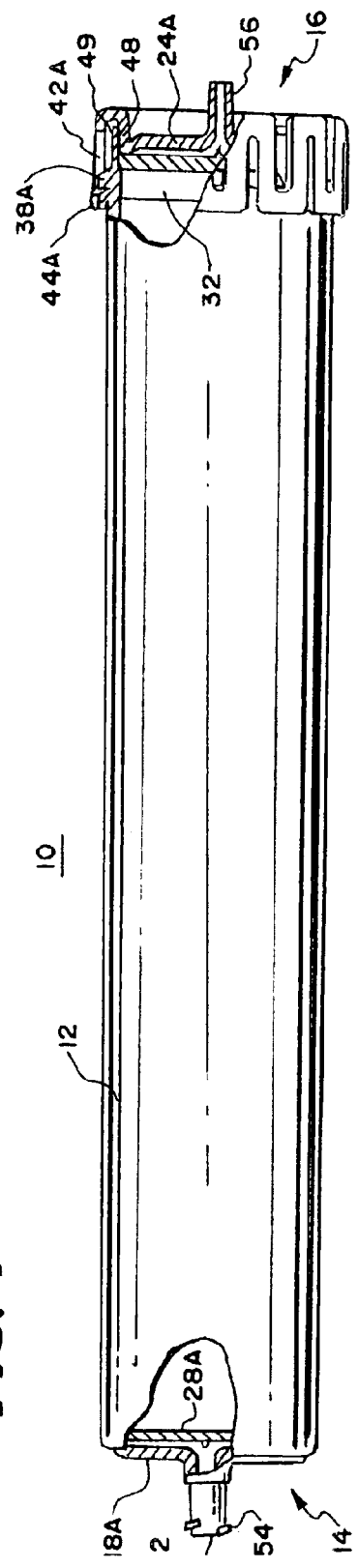
FIG. 4 is a side elevational view partly broken away in sections of the column of FIG. 1.

In FIG. 4, there is shown an elevational view of the column 10 with portions broken away to illustrate the inlet and outlet ends 14 and 16 respectively. As shown in this figure, the filter 28 is mounted against the end of the column body 12 to block packing material 58 from passing into the inlet port 22. A thread 54 is provided for connection to the female lure so as to communicate with a pump and sample injector for chromatography. The columns may be connected in some embodiments to the chromatograph with spring biased connections not requiring high torque turning such as by wrenches to connect the column.

At the outlet end 16, the walls of the column body 12 are tapered. There is shown the tapered rim 49 of the walls of the column body 12 pressed against the tapered walls 48 of the end plate 26 of the snap-on cantilever assembly 20 forming a tight wedge-like seal when the snap-on cantilever assembly 20 is pulled tight to form a fluid tight seal. As shown in this view, the detent 38A holds the snap-on cantilever assembly 20 on tightly by fitting within the opening 44A within the cantilever member 42A.

The inlet and outlet ports 22 and 56 respectively conform to ISO (International Organization for Standardization) 594/1 and 594/2 for 6 percent taper conical fittings but the particular type of fitting is not part of the invention and any suitable inlet and outlet ports may be used. The simple lock fittings were chosen for convenience in attaching and removing the disposable columns by hand.

Figure 5:
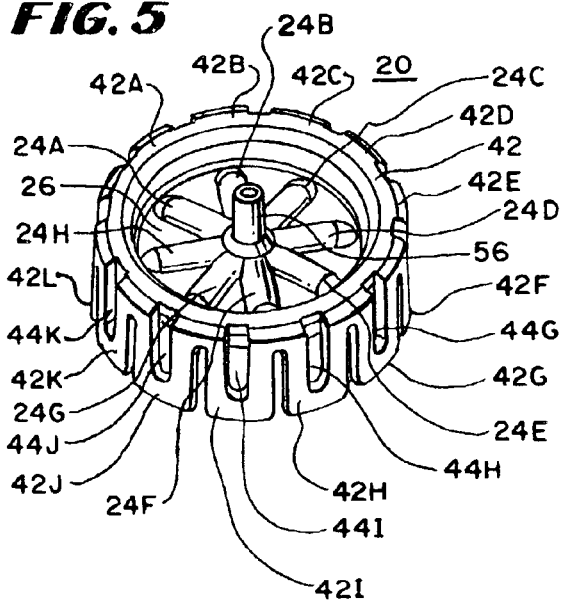
FIG. 5 is a perspective view of a cantilever assembly forming a portion of a snap-fit assembly for the column of FIG. 1.

In FIG. 5, there is shown a perspective view of the cantilever assembly 20 having the cantilever members 42A–42L, each separated by spaces between each cantilever member and central openings 44A–44L (42A–42D being shown). The spaces between cantilever members 42A–42L are picked to reduce bending strain on the bending of the cantilever members 42A–42L consistent with even pressure between the tapered edge of the walls of the column body 12 and the tapered portion of the end plate 26. The central openings 44A–44L are selected in size to keep tensile pressure sufficiently low to prevent failure while reducing bending pressure on the end plate 26. The central outlet port 56 communicates with outlet channels 24A–24H to receive the eluent from the cross-section of the filter 30 and transfer it to the outlet port 56.

Figure 6:
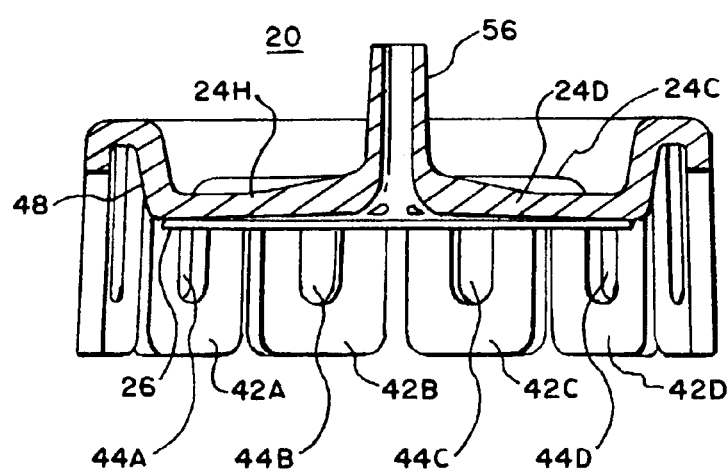
FIG. 6 is a cross-sectional view of the cantilever assembly of FIG. 5.

In FIG. 6, there is shown a cross-sectional view of the snap-on assembly 20 of FIG. 5 showing the cantilever members 42A–42L (42A–42D being shown here) arranged to receive the low end of the ramped detents 38A–38L and be pried outwardly as the walls of the column body 12 (FIG. 4) moves into the cantilever assembly 20 until the ramped detent fits within the corresponding ones of the openings 44A–44L (44A–44D being shown) to hold the cantilever assembly 20 in sealing relationship with the column body 12. As shown in this view, an angled portion in the cantilever members 42A–42D provides a surface 48 for receiving the tapered rim 49 of the end of the walls of the column body 12 (FIG. 4) to form an interference fit to seal the column 10 except for the inlet and outlet ports 14 and 16 respectively.

Figure 7:
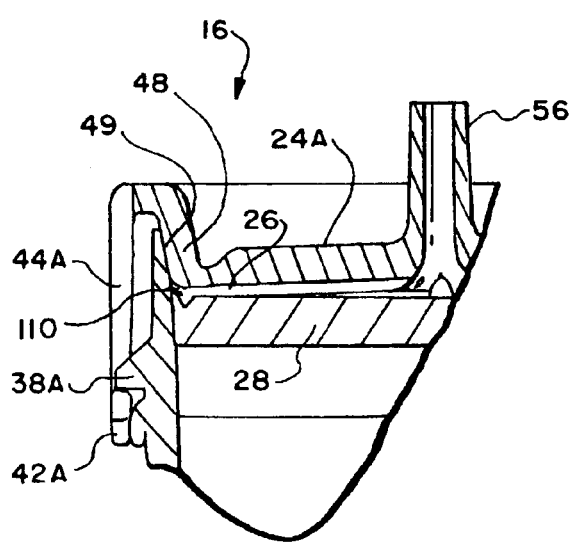
FIG. 7 is an enlarged, fragmentary, sectional view of an end portion of the column showing an interference fit between the end portion and the tubular wall of the column.

In FIG. 7, there is shown a fragmentary, enlarged sectional view of a portion of the outlet end 16 showing the interference fit between the snap-on cantilever assembly 20 and the body wall 12. As shown in this figure, cantilevers 42A is locked onto a detent 38A with the tapered rim 49 of the wall 12 engaging the sloping portion 48 of the wall of the end plate 26 with an interference fit adequate to prevent escape of fluids under the design pressure. The end plate 26 also has a circular ring 110 with a pointed end extending downwardly and contacting the filter 28. The ring 110 is large enough and located close enough to the filter 28 to press into it and form a seal against the passage of material particles. The filter 28 fits against the walls of the column body 12 tightly enough to block the movement of packing material 58 around the filter 28 where it contacts the walls of the column body 12 but, if packing material 58 should be carried onto the outlet port side of the filter 28 because of a poor fit or deformity in the inner wall or in the filter, the ring 110 forms a sufficient seal to prevent the passage of the packing material 58 into the outlet port 56.

Figure 8:
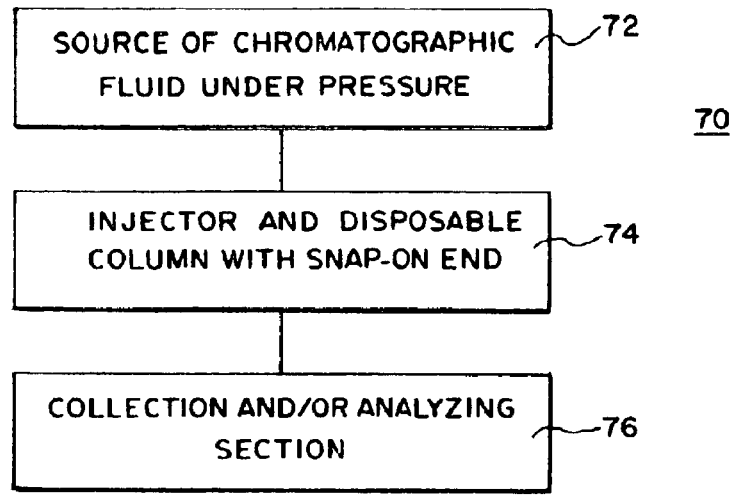
FIG. 8 is a block diagram of a chromatographic system in accordance with the embodiment of the invention.

In FIG. 8, there is shown a chromatographic system 70 having a source of chromatographic fluid under pressure 72, a source of sample, sample injector and disposable column with snap-on end 74 and a collection and or analyzing section 76. The source of chromatographic fluid under pressure 72 supplies fluid to the disposable column 74 through a connection held in place by spring pressure so as not to require threaded connectors that must by tightened or loosened with tool such as wrenches. Sample injected into the column for analysis and/or collection. The eluent for the outlet is supplied to the collection and/or analyzing section for collection for preparatory mounts and analyzing of the liquids as if flows through. The injection and disposable column with snap-on end is designed for high flow through rates and short elution times. The column is intended for one run after which a new column is used although it may last through several runs.

Figure 9:
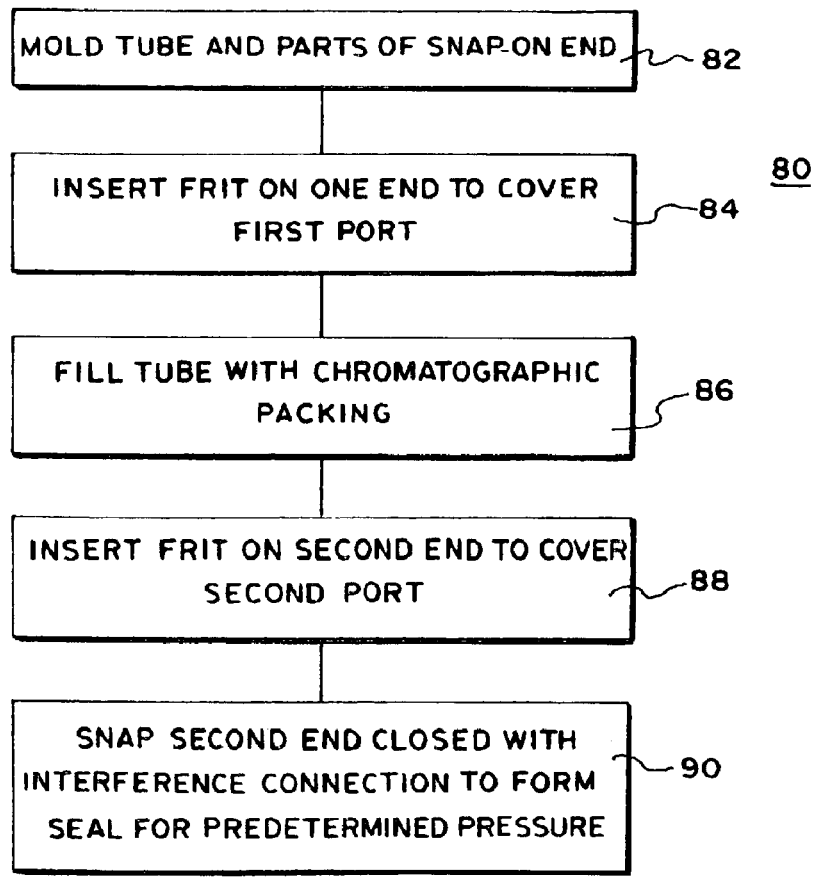
FIG. 9 is a block diagram of a process of assembling a column in accordance with an embodiment of the invention.

In FIG. 9, there is shown a block diagram of a process 80 for forming the column used in the process of FIG. 7. As shown in this figure, the tubular column body 12 of the chromatic column 10 and one end with one of the inlet or outlet ports are molded as a unit as shown in step 82. After the body of the column has been molded, a filter is inserted into the column to rest against the port as shown in step 84. The filter is disk-shaped and has a diameter substantially the same as the inner diameter of the column to prevent packing material from passing through the inlet port and contaminating the system. The filter lies against the panels molded in the inlet side which channel fluid through the inlet port outwardly so as to more uniformly spread the solvent out across the packing material.

When the filter is in place, the tube is filled with chromatographic packing material as shown in step 86 while the tube is inverted with its inlet port down. The packing material is packed uniformly. In the preferred embodiment, this is accomplished by agitating the filled, inverted column and adding packing material if the settled packing material originally inserted falls below the required volume. After being filled with uniform packing material, a second disk-shaped flat filter is place to hold the packing material in place so it does not move into the inlet port as shown in step 88.

Finally, as shown at step 90, the snap-on outlet end is snapped into place so as to provide an interference fit with the walls of the tube and be held with that interference fit by cantilever members and detents. The detents are molded onto the body of the column and the snap-on outlet end has an outlet port with a ring sized to provide an interference fit with the walls. The detents are ramped shaped and the cantilever as they move against them are bent outwardly over the detents and snap over the opposite end at a location in which the ring and the body of the tube for a tight interference fit that will not leak even under the predetermined pressure for the column during operation.

Figure 10:
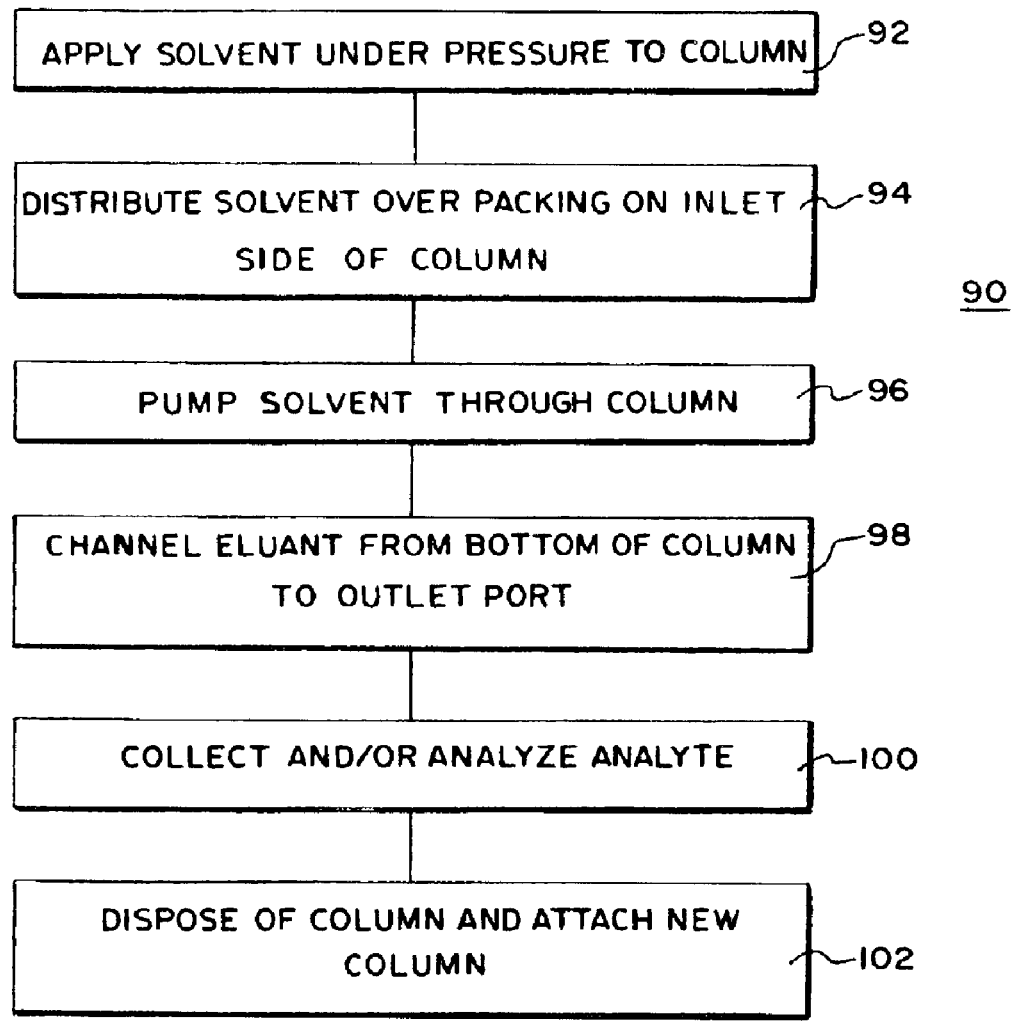
FIG. 10 is a block diagram of a process of using a column in accordance with an embodiment of the invention.

In FIG. 10, there is shown a flow diagram of a process of chromatography utilizing the column 10 of FIG. 1. As shown in FIG. 9, the column when assemble as described in FIG. 7 has solvent applied under pressure as shown at step 92. The solvent is distributed over the inlet end of the packing material by channels through which it flows and which have the side against the packing material open so that the fluid pressure flows the liquid across the filter and then from the filter down into the packing material as shown at step 94.

The solvent is pumped through the column at the selected flow rate for the chromatographic run as shown at step 96 and carries eluent to the bottom of the column where channels opening against the filter channel the fluid evenly to the outlet port so that fluid with a direct flow route through the packing material is flowed rapidly through the channels to the outlet port rather than through the slower radial path of the packing material as shown in step 98. The eluent is then collected and analyzed in a conventional manner as shown at 100. After a number of runs of between one and 10, but preferable 1 run, the column is removed and disposed of as shown at step 102. They are constructed economically so as to render this possible. A new disposable column may then be connected for further chromatographic runs. Typically, runs with the disposable columns are competed in 30 minutes or less and flow rates are 100 milliliters per minute or less. Each run should be completed in 60 minutes or less and average flow rates should be between 25 ml. and 200 ml. per minute.

While a preferred embodiment of the invention has been described with some particularity, many modifications and variations in the invention are possible within the light of the above teaching. Therefore, it is to be understood, that within the scope of the pending claims, the invention may be practiced other than as specifically described.

What is claimed is:

1. A method of manufacturing a chromatographic column comprising the steps of:

molding a column body from plastics;

placing a first filter in a first end having an integrally molded port of the column body and filling the column with packing material up to a second end;

placing a second filter on top of the packing in the second end;

moving a snap-on end with a molded port and the column body together at the second end with linear motion until an interference fit adequate to resist leaks at a value above the rated value of the column is formed.

2. The method of claim 1 in which the step of moving the snap-on end with the molded port onto the column body includes the step of moving walls of the column body and walls of the snap-on end into contact with each other wherein the walls of the column body and the snap-on end are at an angle to each other whereby the walls of the column body and the snap-on end press against each other to form an interference fit.

3. The method of claim 2 wherein at least one of the walls of the column body and the snap-on end have an angled portion that engages with the other of the walls of the column body and the snap-on end.

4. The method of claim 1 wherein the step of moving includes the steps of:

moving one of the walls of the column body and the walls of the snap-on end with a flexible member and one of the walls of the column body and the walls of the snap-on end with a detent together whereby the flexible member is bent by the detent; and holding the walls of the column body and the walls of the snap-on end together with an interference fit.

5. The method of claim 1 in which the step of filling the column with packing material includes the step of vibrating the column to evenly distribute the packing material.

6. The method of claim 1 in which the step of inserting the end on the column with an interference fit includes the step of inserting the end on the column with straight linear motion while cantilever members are bent outwardly until they are caught on a catch.

7. The method of claim 1 in which at least some of the steps of placing a filter and filling the column are done automatically.

8. The method of claim 1 further including the step of:

molding the snap-on end;

the steps of molding the snap-on end and the step of molding the body comprising the steps of forming a plurality of cantilever members onto one of the column body and the snap-on end and forming a plurality of detents onto the other of the body and snap-on end;

the number of detents and cantilever members being selected so as to maintain bending stress of the cantilever members that are being bent outwardly over the catch below a value of failure stress of a material comprising the cantilever members.

9. The method of claim 1 in which the distance of overlapping of the angled portion of contact between the end member and the walls of the column body is sufficient to create an interference fit capable of withstanding a pressure higher than an operating pressure of the column.

10. The method of claim 9 in which the distance of overlap is determined by a distance between the detents and a rim near an edge of the wall of the column body.

11. The method of claim 1 wherein at least one of the steps of molding the body and molding the snap-on end comprises the step of molding an end member integrally with the walls of a tubular body.

12. The method of claim 1 wherein the step of moving the snap-on end comprises the step of snapping the snap-on end in place onto the body walls after the packing has been placed into the column and before solvent is caused to flow into an inlet port.

13. The method of claim 1 wherein at least one of the steps of molding the body and molding the snap-on end includes the step of molding at least one of the inlet and outlet ports integrally with a corresponding one of inlet and outlet end members.

* * * * *